US010315353B1

(12) United States Patent
Culp et al.

(10) Patent No.: US 10,315,353 B1
(45) Date of Patent: Jun. 11, 2019

(54) SYSTEMS AND METHODS FOR THERMOFORMING DENTAL ALIGNERS

(71) Applicant: SmileDirectClub LLC, Nashville, TN (US)

(72) Inventors: Clete Culp, Nashville, TN (US); Christopher Yancey, Nashville, TN (US); John Dargis, Nashville, TN (US); Mark French, Nashville, TN (US); Daniel Pfeffer, Nashville, TN (US); Steve Cicurel, Nashville, TN (US)

(73) Assignee: SmileDirectClub LLC, Nashville, TN (US)

( * ) Notice: Subject to any disclaimer, the term of this patent is extended or adjusted under 35 U.S.C. 154(b) by 0 days.

(21) Appl. No.: 16/188,570

(22) Filed: Nov. 13, 2018

(51) Int. Cl.
| B29C 51/02 | (2006.01) |
| B29C 51/24 | (2006.01) |
| B29C 51/42 | (2006.01) |
| B29C 51/26 | (2006.01) |
| B29C 51/46 | (2006.01) |
| A61C 7/08 | (2006.01) |
| B29K 23/00 | (2006.01) |

(52) U.S. Cl.
CPC .............. *B29C 51/24* (2013.01); *B29C 51/02* (2013.01); *B29C 51/261* (2013.01); *B29C 51/421* (2013.01); *B29C 51/46* (2013.01); *A61C 7/08* (2013.01); *B29K 2023/10* (2013.01)

(58) Field of Classification Search
CPC .......... B29C 51/24; B29C 51/02; B29C 51/46; B29C 51/421; B29C 51/261
See application file for complete search history.

(56) References Cited

U.S. PATENT DOCUMENTS

| 3,688,963 | A | * | 9/1972 | Snow | B29C 51/261 226/162 |
| 4,687,612 | A | * | 8/1987 | Clarke | B29B 13/023 264/322 |
| 5,806,745 | A | * | 9/1998 | Irwin | B29C 51/261 219/388 |
| 8,083,976 | B2 | * | 12/2011 | Lengsfeld | B29C 70/504 156/199 |
| 8,888,480 | B2 | * | 11/2014 | Yoo | B33Y 10/00 425/375 |

(Continued)

*Primary Examiner* — Nahida Sultana
(74) *Attorney, Agent, or Firm* — Foley & Lardner LLP

(57) ABSTRACT

A system includes a heating system, a forming system, a conveyor system, and a plurality of thermoforming assemblies for supporting a dental mold and a thermoforming material. The heating system includes a first heater to heat the thermoforming material when proximate the first heater, a second heater configured to heat the thermoforming material when proximate the second heater, and a temperature sensor to detect a temperature of the thermoforming material when the thermoforming material is proximate either of the first heater and the second heater. The forming system includes an actuator and a pressure system to compress the heated thermoforming material to the dental mold. The conveyor system moves the plurality of thermoforming assemblies in a stepwise movement sequence from a loading area to the heating system, from the heating system to the forming system, and from the forming system to an unloading area.

20 Claims, 8 Drawing Sheets

(56) References Cited

U.S. PATENT DOCUMENTS

| | | | |
|---|---|---|---|
| 2011/0003025 A1* | 1/2011 | Patel | B29C 51/08 |
| | | | 425/504 |
| 2015/0013688 A1* | 1/2015 | Frantz | B29C 51/14 |
| | | | 128/848 |
| 2016/0106572 A1* | 4/2016 | Frantz | B29C 69/001 |
| | | | 128/848 |
| 2017/0144360 A1* | 5/2017 | Moore, III | B29C 51/18 |

* cited by examiner

SYSTEMS AND METHODS FOR THERMOFORMING DENTAL ALIGNERS

BACKGROUND

The present disclosure relates generally to dental aligners. More specifically, the present disclosure relates to thermoforming dental aligners.

Dental aligners for positioning teeth can be thermoformed over positive molds of a person's teeth that depict a repositioned state of the person's teeth. Such a thermoforming process typically involves heating a material and then pressure molding the material onto the positive mold. However, traditional processes for thermoforming dental aligners are usually labor intensive and require a person to manually manipulate positive molds and materials throughout the thermoforming process. For example, some thermoforming processes may require a technician to insert a positive mold including thermoforming material into a heating chamber to heat the thermoforming material, and then to move the positive mold and thermoforming material to a forming chamber to thermoform the thermoforming material to the positive mold.

Positive molds for the thermoforming process can be created from a negative dental impression or a digital scan of the person's teeth. For example, to take a dental impression, a dental tray having a viscous, thixotropic impression material therein is fit over the dental arches of the person, and the impression material sets to a solid thereby leaving an imprint of the structures in the person's mouth. When removed from the mouth, the impression provides a detailed and stable negative of the person's teeth. Such a process has traditionally been performed in a dental office under the supervision of a dental professional, and therefore requires significant time and inconvenience. Further complicating the process, the dental office delivers the impressions to an outside vendor for manufacturing dental aligners, which can result in the person having to revisit the dental office to retake impressions or digital scans if any errors are discovered, such as an incomplete or inaccurate impression of the person's teeth and tissues.

SUMMARY

An embodiment relates to a system including a plurality of thermoforming assemblies, a heating system, a forming system, and a conveyor system. The plurality of thermoforming assemblies are each configured to support a dental mold and a thermoforming material. The heating system includes a first heater, a second heater, and a temperature sensor. The first heater is configured to heat the thermoforming material when the thermoforming material is proximate the first heater. The second heater is configured to heat the thermoforming material when the thermoforming material is proximate the second heater. The temperature sensor is arranged to detect a temperature of the thermoforming material when the thermoforming material is proximate either of the first heater and the second heater. The forming system includes an actuator and a pressure system. The actuator is configured to form a chamber encompassing the dental mold and a portion of the heated thermoforming material. The pressure system is configured to pressurize the chamber to compress the heated thermoforming material to the dental mold. The conveyor system is configured to move the plurality of thermoforming assemblies in a stepwise movement sequence from a loading area to the heating system, then from the heating system to the forming system, and then from the forming system to an unloading area. Each stepwise movement of the thermoforming assemblies is based on a temperature of a first thermoforming material of a first thermoforming assembly at the first heater and a temperature of a second thermoforming material of a second thermoforming assembly at the second heater.

Another embodiment relates to a system including a controller configured to control a conveyor system to move a thermoforming assembly in a stepwise movement sequence. The thermoforming assembly includes a dental mold and a thermoforming material. The stepwise movement sequence includes moving the assembly in sequence to a first predetermined position proximate a first heater, then to a second predetermined position proximate a second heater, then to a third predetermined position proximate a forming system. The thermoforming assembly remains at each predetermined position for a predetermined time. The controller is further configured to control the first heater to heat the thermoforming material above a first temperature threshold or within a first temperature range, control the second heater to heat the thermoforming material above a second temperature threshold or within a second temperature range, and control the forming system to compress the heated thermoforming material to the dental mold to form a shape of a dental aligner based on the thermoforming material being above a forming temperature threshold or within a forming temperature range.

Another embodiment relates to a method including determining, based on data from a temperature sensor configured to detect a temperature of a thermoforming material at a first heater of a heating system, that the temperature of the thermoforming material meets a first temperature requirement while a thermoforming assembly including the thermoforming material and a dental mold is located at the first heater. The method further includes controlling a conveyor system coupled with the thermoforming assembly to advance the thermoforming assembly from the first heater to a second heater of the heating system. The method further includes determining, based on data from the temperature sensor, that the temperature of the thermoforming material meets a second temperature requirement while the thermoforming assembly is located at the second heater. The method further includes controlling the conveyor system to advance the thermoforming assembly from the second heater to a forming system. The method further includes controlling a forming system including an actuator and a pressure system to apply pressure to an upper portion of a chamber around the dental mold and at least a portion of the thermoforming material to compress the thermoforming material to the dental mold.

Another embodiment relates to a system including a first thermoforming system, a second thermoforming system, and a third thermoforming system. The first thermoforming system includes a first heating system and a first forming system. The first heating system is configured to heat a first thermoforming material above a first temperature threshold or within a first temperature range. The first forming system is configured to compress the first thermoforming material to a dental mold to form a first dental aligner having a first hardness or first thickness. The second thermoforming system includes a second heating system and a second forming system. The second heating system is configured to heat a second thermoforming material above a second temperature threshold or within a second temperature range. The second forming system is configured to compress the second thermoforming material to the dental mold to form a second dental aligner having a second hardness or second thickness.

The third thermoforming system includes a third heating system and a third forming system. The third heating system is configured to heat a third thermoforming material above a third temperature threshold or within a third temperature range. The third forming system is configured to compress the third thermoforming material to the dental mold to form a third dental aligner having a third hardness or third thickness.

This summary is illustrative only and is not intended to be in any way limiting. Other aspects, inventive features, and advantages of the devices or processes described herein will become apparent in the detailed description set forth herein, taken in conjunction with the accompanying figures, wherein like reference numerals refer to like elements.

DETAILED DESCRIPTION

Before turning to the figures, which illustrate certain exemplary embodiments in detail, it should be understood that the present disclosure is not limited to the details or methodology set forth in the description or illustrated in the figures. It should also be understood that the terminology used herein is for the purpose of description only and should not be regarded as limiting.

Referring generally to the figures, described herein are systems and methods for thermoforming dental aligners. A motorized belt is rotatable between a first belt-transfer device, a heating station, a forming station, and a second belt-transfer device. The belt includes cleats that may form a bay for receiving a thermoforming assembly. The heating station includes a plurality of heaters including a first heater and a second heater. A temperature sensor is arranged to detect a temperature of thermoforming material located proximate a dental mold located on the thermoforming assembly. The thermoforming assembly with the thermoforming material is moved from the first heater to the second heater after the temperature of the thermoforming material meets a first threshold, and from the second heater to the forming station after the temperature of the thermoforming material meets a second threshold. An actuator and a pressure assembly are controlled to apply pressure to an upper portion of a chamber around the heated thermoforming material and the dental mold to compress the thermoforming material to the dental mold.

The embodiments described herein provide for automated or semi-automated manufacturing of dental aligners. While the systems and methods disclosed herein specifically relate to or reference the fabrication of dental aligners, it will be appreciated that the systems and methods disclosed herein could also be used to create retainers, night guards, or other dental devices by thermoforming materials over a dental mold. The embodiments disclosed herein may increase the consistency and production of dental aligners. Furthermore, such embodiments may decrease the likelihood of human error. For instance, in the embodiments described herein, operator intervention and input is minimized, thus lessening operator exposure and any resulting human error. It will also be appreciated that operator intervention can be even further minimized as operator actions can be further automated. The embodiments described herein may rapidly output dental aligners as compared to manually generating dental aligners on an individual basis. Various other advantages may become apparent based on the following description.

Figure 1:
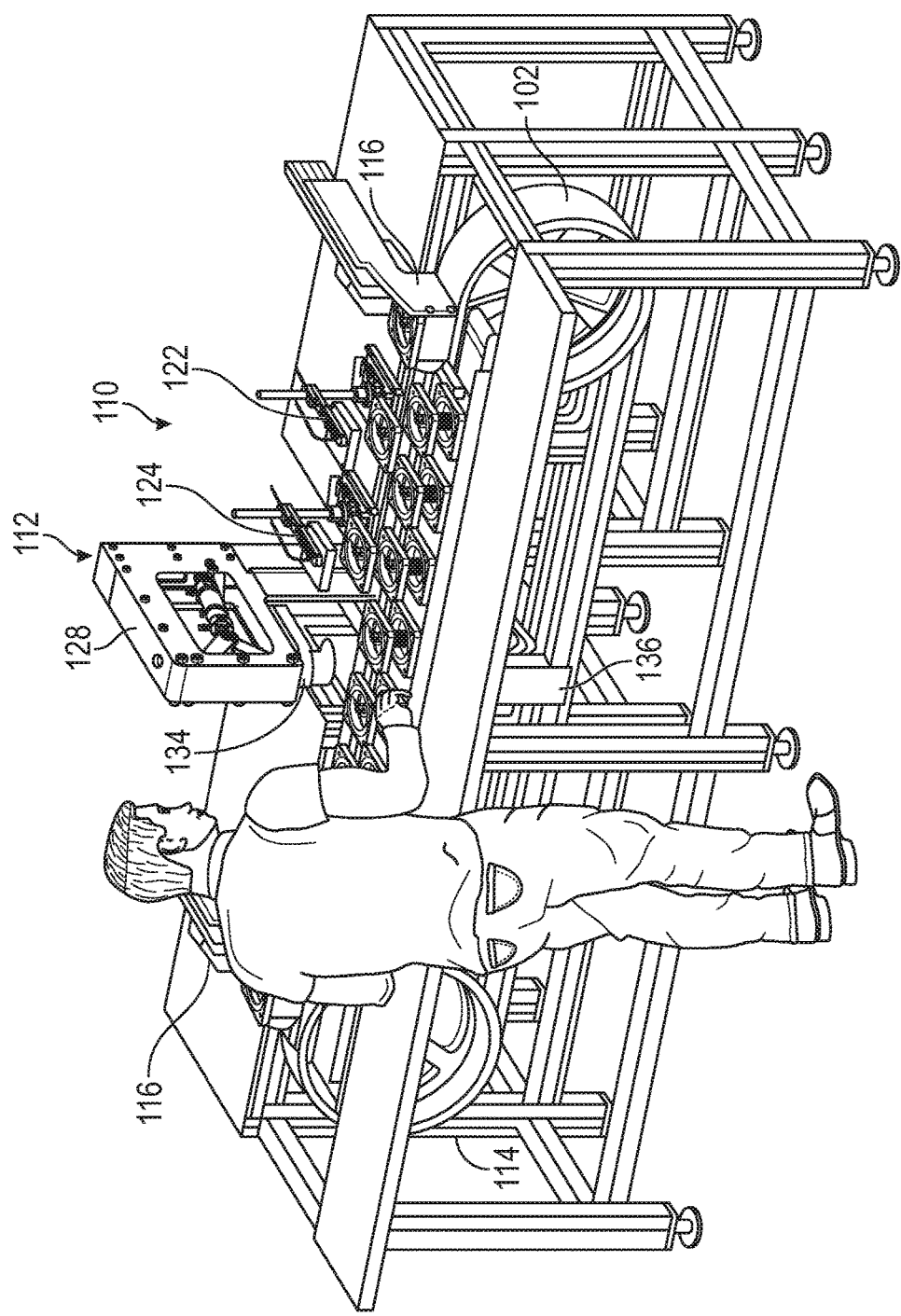
FIG. 1 is an illustration of a system for thermoforming dental aligners including a first motorized belt and a second motorized belt, according to an exemplary embodiment.
Figure 2:
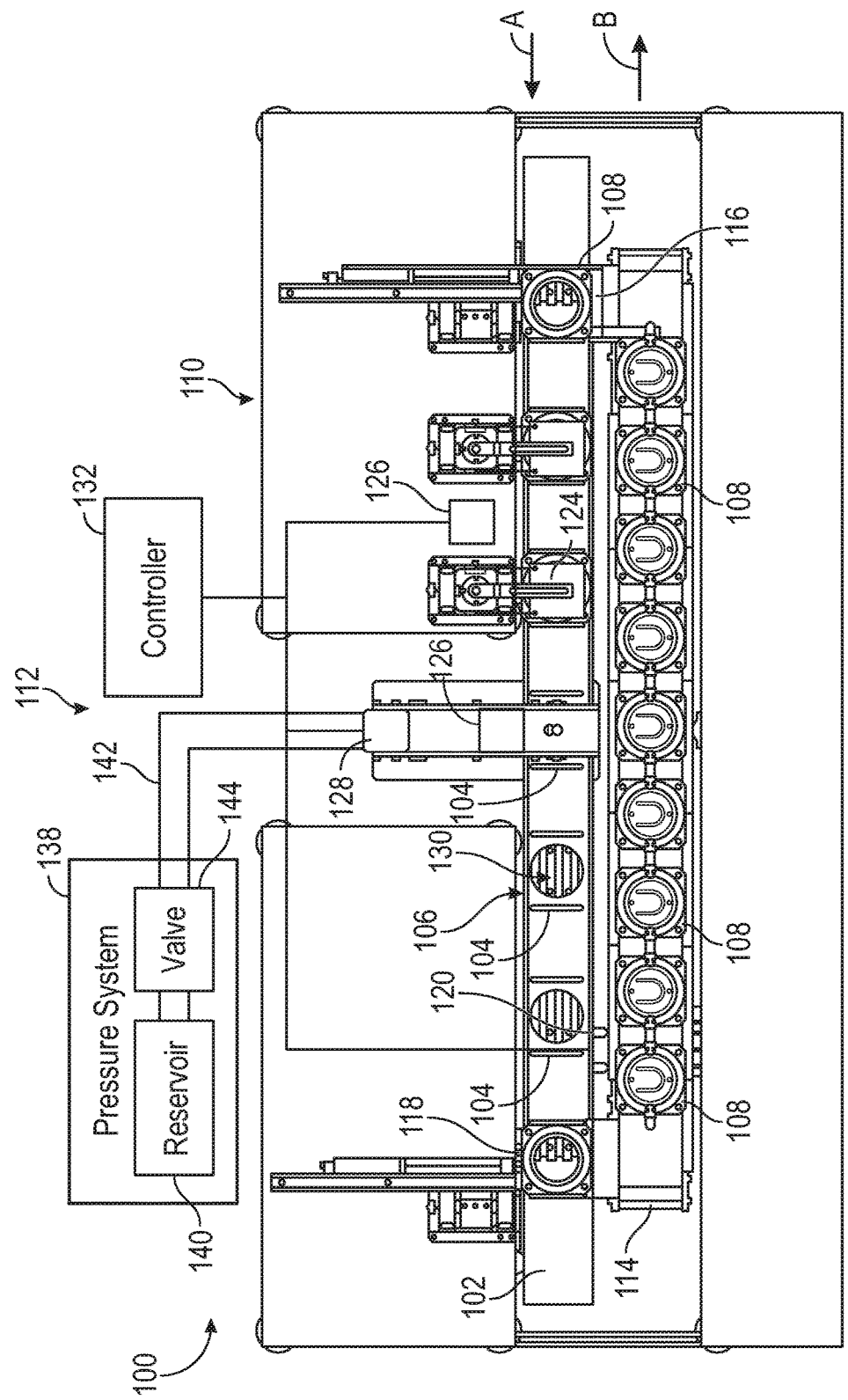
FIG. 2 is a top plan view of the system for thermoforming dental aligners of FIG. 1, according to an exemplary embodiment.
Figure 3:
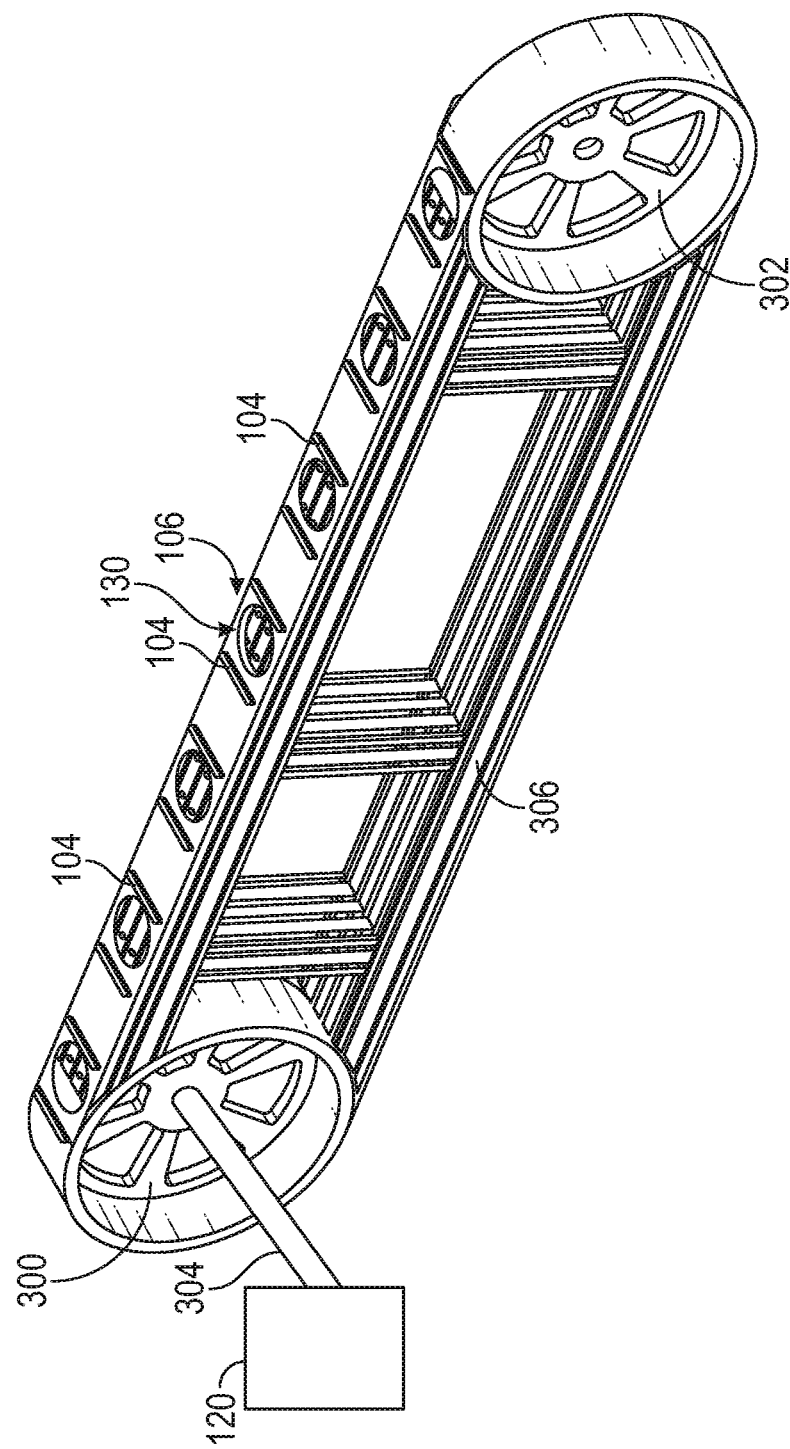
FIG. 3 is an isolated view of the first motorized belt of the system of FIG. 1, according to an exemplary embodiment.

Referring now to FIG. 1-FIG. 3, an embodiment of a system 100 for thermoforming dental aligners is shown. Specifically, FIG. 1 and FIG. 2 are illustrations of the overall system 100 for thermoforming dental aligners, and FIG. 3 is an illustration of an isolated view of a first motorized belt 102 of the system 100, according to an exemplary embodiment. The system 100 is shown to include a first motorized belt 102 configured to rotate in a first direction A. The system is also shown to include a second motorized belt 114 configured to rotate in a second direction B. In some embodiments, the first direction A and second direction B may be parallel and opposite to one another. The first motorized belt 102 may also be referred to herein as a thermoforming belt, and the second motorized belt 114 may also be referred to as a loading belt.

The first motorized belt 102 may include a plurality of cleats 104 which extend perpendicular with respect to the first direction A on the first motorized belt 102. The cleats 104 form a bay 106 for receiving a thermoforming assembly 108. The first motorized belt 102 is configured to rotate between a heating station 110 and a forming station 112. The first motorized belt 102 is driven by a motor 120. For instance, the first motorized belt 102 generally includes a pulley system including a first pulley 300 and a second pulley 302. The first pulley 300 is driven by the motor 120 (as shown in FIG. 3) via a shaft 304 extending between and coupling the motor 120 to the pulley 300. The first motorized belt 102 is shown to include a supporting frame structure 306 to maintain the rigidity of the first motorized belt 102. As the motor 120 drives the pulley 300, the first motorized belt 102 rotates (e.g., with the first pulley 300), which in turn causes rotation of the second pulley 302. While only the first motorized belt 102 is shown in FIG. 3, it will be appreciated that the second motorized belt 114 can be similarly constructed and operated as the first motorized belt 102. For example, the second motorized belt 114 can be driven separate from the first motorized belt 102 or be driven by the same motor 120 of the first motorized belt 102. In some embodiments, the first motorized belt 102 can drive the second motorized belt 114, or the second motorized belt 114 can drive the first motorized belt 102.

Figure 4:
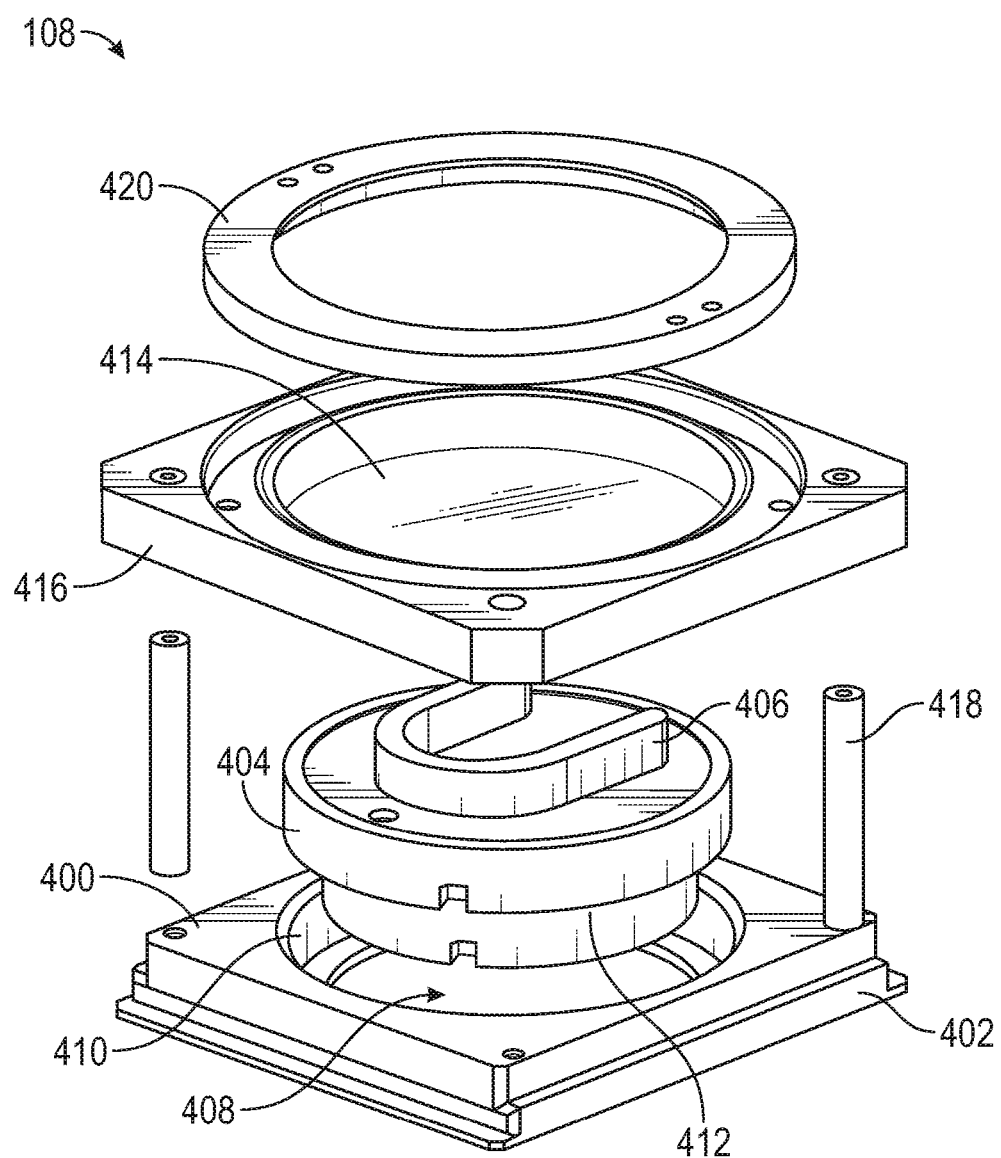
FIG. 4 is an illustration of a thermoforming assembly of the system of FIG. 1, according to an exemplary embodiment.

The thermoforming assembly 108 is assembled (e.g., as shown in FIG. 4) by an operator, for instance, and positioned on the belt system, comprising the first motorized belt 102 and the second motorized below 114 (e.g., between the cleats 104). In some embodiments, the thermoforming assembly 108 is not removed from the belt system by the operator. Rather, only the thermoforming material 414 and the mold 406 are removed and added to the thermoforming assembly 108 as part of the thermoforming process (e.g., the thermoforming assembly 108 is secured or removably secured in place via the cleats 104).

As described in greater detail below, the thermoforming assembly 108 is configured to support, retain, hold, or otherwise carry thermoforming material 414 and a dental mold 406. The first motorized belt 102 carries the thermoforming assembly 108 (including the thermoforming material 414 and dental mold 406) to the heating station 110 and the forming station 112. The thermoforming material 414 is heated at the heating station 110. An upper chamber structure 134 at the forming station 112 engages with a dental mold nest 404 of the thermoforming assembly 108 to form a chamber. The upper chamber structure 134 downwardly towards the dental mold nest 404, which is lifted up towards the thermoforming material 414 by a lifting device 136. The upper chamber structure 134 and dental mold nest 404 sandwich the thermoforming material 414 to form a seal (thus eliminating the need for any other sealing structure such as an O-ring). Air is removed from the chamber or applied (e.g., by a pressure system that includes a vacuum) inside the chamber structure 134 which causes the thermoforming material 414 to form onto the mold. When the thermoforming material 414 is thermoformed to the dental mold 406, the thermoforming material 414 may be used as a dental aligner by a user for repositioning the user's teeth. For instance, the thermoformed thermoforming materials (e.g., referred to hereinafter as the dental aligners) are trimmed for comfort, sent to the user, and positioned by the user in the user's mouth for repositioning the user's teeth.

Referring now to FIG. 1 and FIG. 4, the thermoforming assembly 108 may include various components and elements for thermoforming thermoforming material 414 to a dental mold 406. Specifically, FIG. 4 depicts an embodiment of a thermoforming assembly 108 of the system 100, according to an exemplary embodiment. The thermoforming assembly 108 includes a supporting surface 400. The supporting surface 400 includes notches 402 configured to slide between the cleats 104. For instance, the cleats 104 can include lips 800 (of FIG. 8) sized to extend over the notches 402. The supporting surface 400 may slide between the cleats 104 with the notches 402 engaging the lips 800 of the cleats 104.

The supporting surface 400 is shown to include a dental mold nest 404. The dental mold nest 404 is configured to receive a dental mold 406 (e.g., a mold of an impression, model, or other three-dimensional representation of a person's dental arch). The dental mold nest 404 is tooled, designed, or configured to receive the dental mold 406. As one example, the dental mold nest 404 may include a tooled portion configured to receive and secure the dental mold 405. The dental mold nest 404 is inserted into and rests upon the supporting surface 400. For instance, the supporting surface 400 is shown to include an opening 408. The dental mold nest 404 rests within the opening 408. The opening 408 is shown to include features 410 (e.g., ledges, notches, etc.) along the interior surface of the opening 408 which engage with features 412 on an exterior surface of the mold nest 304 (e.g., corresponding ledges, extensions, etc.). The dental mold nest 404 is positioned within the opening 408 such that the dental mold 406 is positioned upwardly on the thermoforming assembly 108.

The thermoforming assembly 108 may also include thermoforming material 414. The thermoforming material 414 may be any type of material capable of being thermoformed, such as a polymeric material (e.g., plastic) configured to be heated for changing a surface contour of the polymeric material. The thermoforming material 414 may be retained within a thermoforming material nest 416 positioned above the dental mold nest 404 (e.g., by separators 418). In some embodiments, the thermoforming material nest 416 may include a recession or recessed portion which is sized to receive the thermoforming material 414. The recessed portion may prevent lateral movement of the thermoforming material 414 during transportation, heating, and thermoforming.

The thermoforming material 414 may be retained within the thermoforming material nest 416 via a retaining ring 420. In some embodiments, the retaining ring 420 may be constructed of or include magnetic material, and the thermoforming material nest 416 may also be constructed of or include magnetic material. In some embodiments, the retaining ring 420 may include a different type of locking mechanism, such as fasteners, pins, clips, etc. The retaining ring 420 may be coupled to the thermoforming material nest 416 to prevent or inhibit the thermoforming material 414 moving within the thermoforming material nest 416. Where magnetic material is used, the magnetic material for the retaining ring 420 may interact with the magnetic material in the thermoforming material nest 416 to magnetically couple the retaining ring 220 to the thermoforming material nest 416. The thermoforming material 414 may be sandwiched between the retaining ring 420 and thermoforming material nest 416, thus locking, retaining, or otherwise maintaining the position of the thermoforming material 414 in the thermoforming material nest 416. While magnetic material is described in the above embodiments, in other embodiments, the thermoforming material 414 may be locked, retained, or otherwise be maintained in the thermoforming material nest 416 in a number of different ways, such as with screws, clips, etc.

Referring back to FIG. 1 and FIG. 2, the thermoforming assemblies 108 may be loaded by an operator. The thermoforming assemblies 108 may be maintained in a clean, sterile environment (e.g., in a clean room) to eliminate, control, or otherwise inhibit or prevent dust, particulates or other contamination which may affect the integrity of the dental aligners. The operator may assemble the thermoforming assemblies 108 (e.g., as shown in FIG. 4). The operator may assemble the thermoforming assemblies 108 on the second motorized belt 114 (e.g., the loading belt). As stated above, the second motorized belt 114 may rotate substantially parallel to (e.g., along the direction A) the first motorized belt 102 (e.g., the primary motorized belt), but in the opposite direction (e.g., in the direction B).

Figure 6:
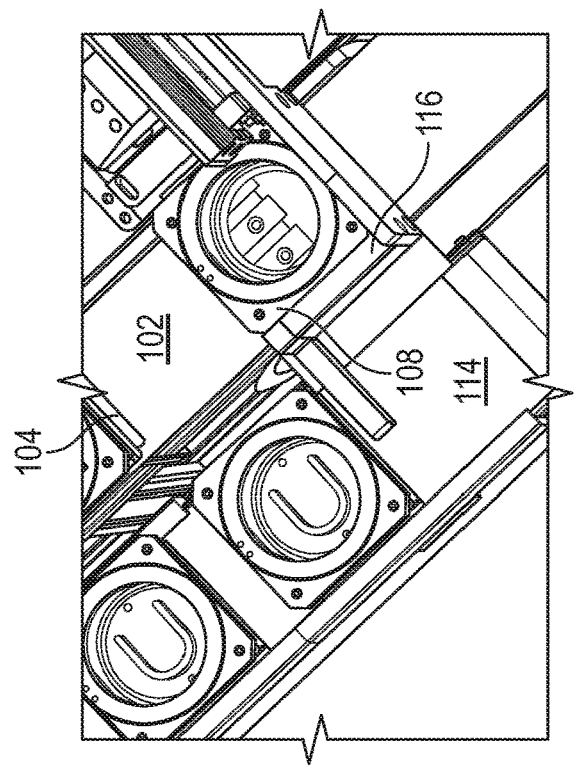
FIG. 6 is an illustration of the first transfer device of FIG. 5 shown in a post-transfer position, according to an exemplary embodiment.
Figure 5:
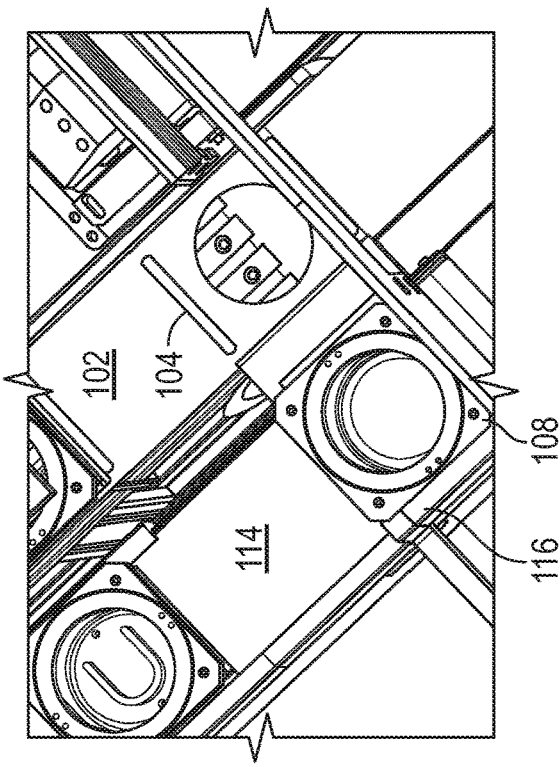
FIG. 5 is an illustration of a first transfer device for transferring the thermoforming assembly of FIG. 4 from the first motorized belt to the second motorized belt of FIG. 3, shown in a pre-transfer position, according to an exemplary embodiment.
Figure 8:
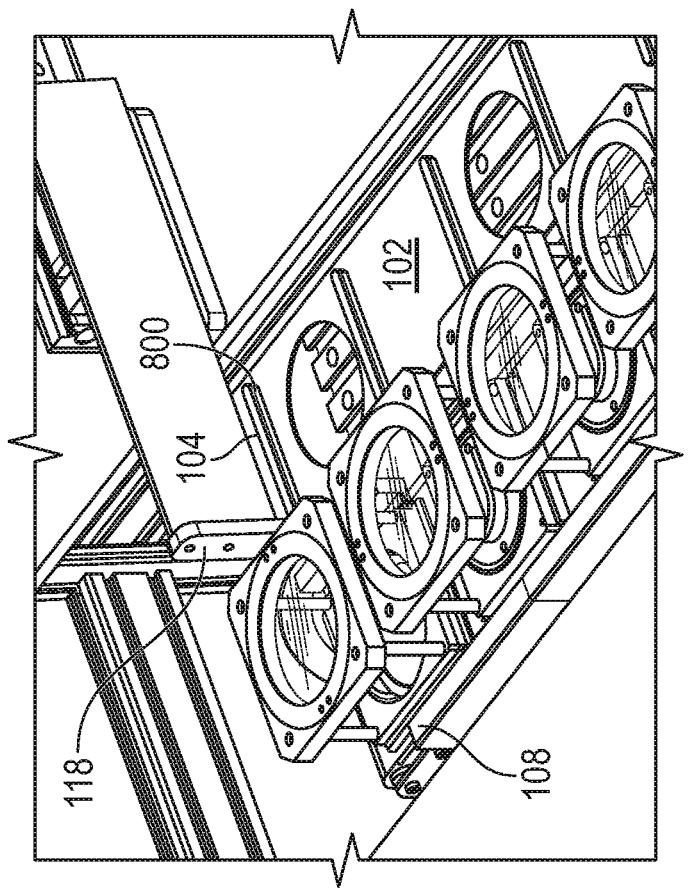
FIG. 8 is an illustration of the second transfer device of FIG. 7 shown in a post-transfer position, according to an exemplary embodiment.
Figure 7:
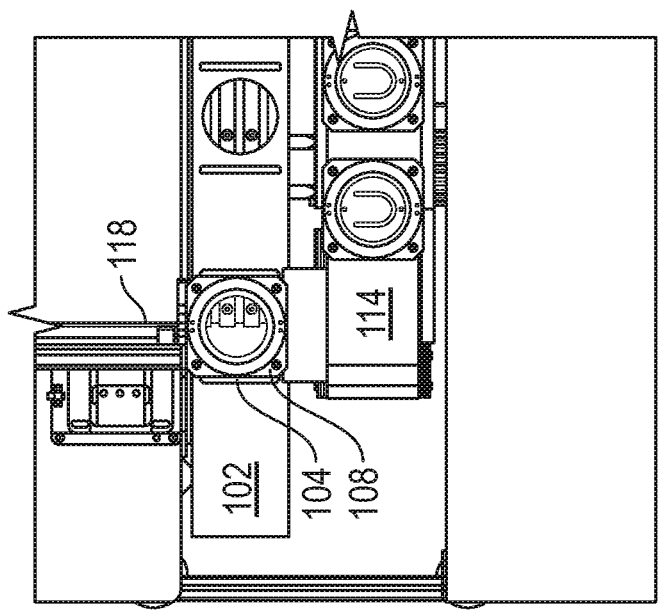
FIG. 7 is an illustration of a second transfer device for transferring the thermoforming assembly of FIG. 4 from the second motorized belt of FIG. 3 to the first motorized belt, shown in a pre-transfer position, according to an exemplary embodiment.

Referring now to FIG. 1 and FIGS. 5-8, in some embodiments, the system 100 includes transfer devices 116, 118 for transferring loaded thermoforming assemblies 108 from the second motorized belt 114 to the first motorized belt 102, and for transferring thermoforming assemblies 108 with thermoforming material 414 that has undergone thermoforming from the first motorized belt 102 to the second motorized belt 114, respectively. Specifically, a transfer device 116 is shown in FIG. 5-6 for transferring loaded thermoforming assemblies 108 from the second motorized belt 114 to the first motorized belt 102. A transfer device 118 is shown in FIG. 7-8 for transferring thermoforming assemblies 108 with thermoforming material 414 that has undergone thermoforming from the first motorized belt 102 to the second motorized belt 114. In some embodiments, the transfer devices 116, 118 may have aspects similar to one another. The transfer devices 116, 118 engage a thermoforming assembly 108 when the thermoforming assembly 108 is positioned at the end of the first motorized belt 102 and second motorized belt 114 (e.g., the positions shown in FIGs. 5-6 and FIGs. 7-8, respectively). The transfer devices 116, 118 slide the thermoforming assembly 108 between the first motorized belt 102 and second motorized belt 114. As can be best seen in FIG. 8, the notches 402 (shown in FIG. 3) of the thermoforming assembly 108 slide between the lips 800 of the cleats 104. The transfer devices 116, 118 slide the thermoforming assembly 108 between the first motorized belt 102 and the second motorized belt 114 such that the thermoforming assembly 108 is maintained between cleats 104, or in transit between cleats 104 of the different motorized belts. In some embodiments, the thermoforming assembly 108 may generally not be removable within the system 100. Hence, the first motorized belt 102, second motorized belt 114, and transfer devices 116, 118 generally cause the thermoforming assemblies 108 to rotate in a circle through the system 100. In this embodiment, the thermoforming assemblies 108 are loaded, unloaded, and re-loaded with dental molds 406, thermoforming material 414, etc., without being transferred between different belts.

Referring back to FIG. 1, in some embodiments, the first motorized belt 102 and the second motorized belt 114 may be rotated, driven, etc. by the same motor 120 (e.g., an electric motor, engine, etc.). The first motorized belt 102 and the second motorized belt 114 may be driven by the same motor 120 such that the belts 102, 114 are driven at the same speed and advance in the same stages as one another. Hence, the motor 120 may advance the belts 102, 114 step wise between various stations. In driving the belts 102, 114 at the same speed and in the same stages, thermoforming assemblies 108 may correspondingly be advanced together (e.g., in unison), thus eliminating or lessening the likelihood of bottlenecks. In such an embodiment, the belts 102, 114 are not continuously driven such that the belts 102, 114 do not continuously move.

Figure 9:
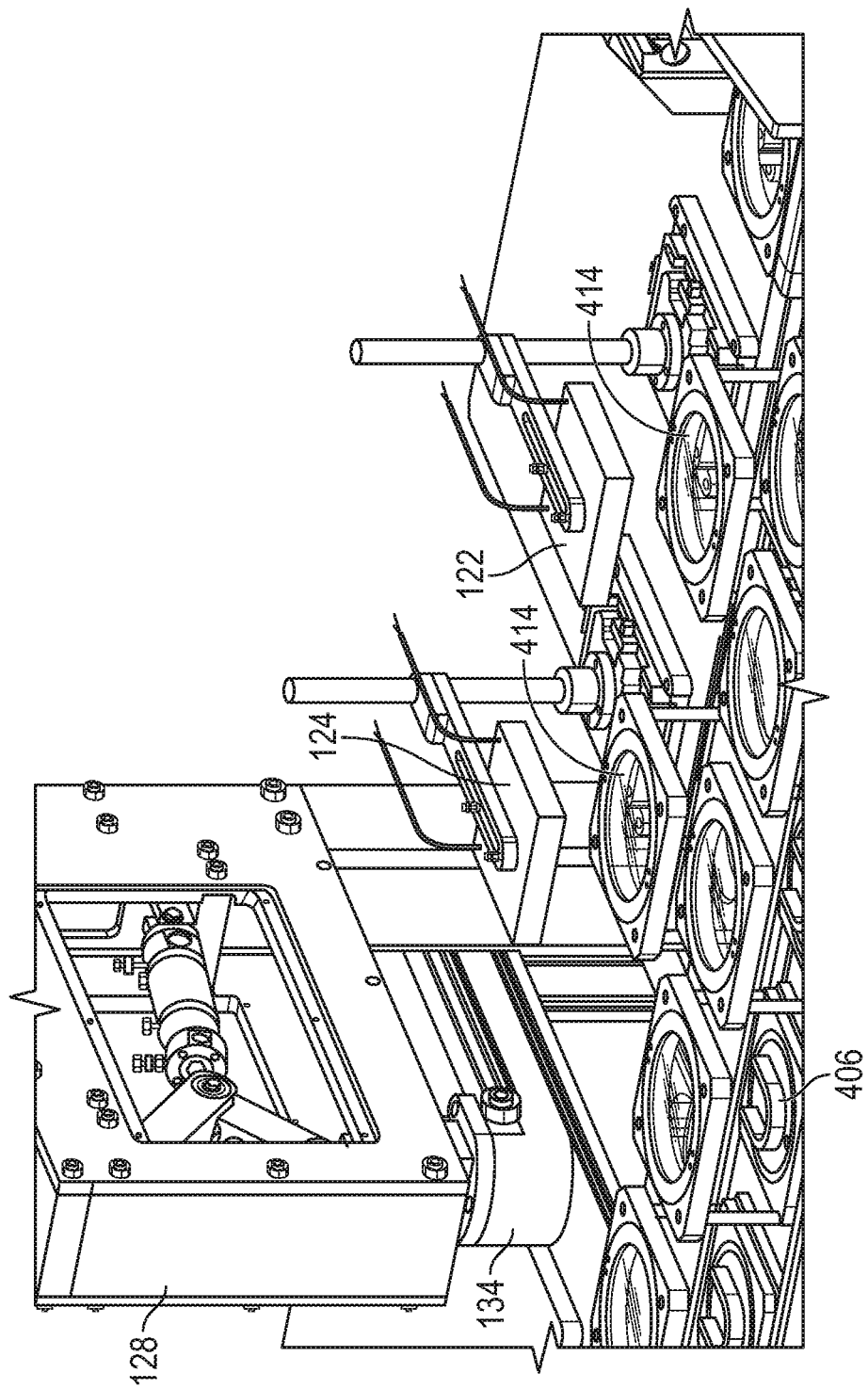
FIG. 9 is a perspective view of a heating station of the system of FIG. 1, according to an exemplary embodiment.

Referring now to FIG. 1 and FIG. 9, the heating station 110 may include a plurality of heaters including a first heater 122 and a second heater 124. Specifically, FIG. 9 shows a perspective view of the heating station 110, according to an exemplary embodiment. While two heaters are shown and described herein, in various embodiments, the heating station 110 may include more or fewer heaters. Accordingly, the present disclosure is not limited to two heaters, and may include or otherwise incorporate any number of heaters. The heaters 122, 124 supply, provide, or otherwise output heat, such as inductive heat, convective heat, etc. The heaters 122, 124 heat the thermoforming material 414 when the thermoforming assembly 108 is positioned proximate (such as beneath) the heaters 122, 124. The thermoforming assemblies 108 advance to a position underneath the first heater 122 and pause for heating by the first heater 122. Next, the thermoforming assemblies 108 advance from the first heater 122 to the second heater 124 and pause for heating by the second heater 124. Next, the thermoforming assemblies 108 advance from the second heater 124 to the forming station 112, as discussed in greater detail below. As one thermoforming assembly 108 advances from the first heater 122 to the second heater 124, another thermoforming assembly 108 may advance to the position underneath the first heater 122.

The heaters 122, 124 are shown to be suspended above the thermoforming assemblies 108, as can be best seen in FIG. 2. The heaters 122, 124 supply heat to the thermoforming material 414. The heating station 110 includes at least one temperature sensor 126. The temperature sensors 126 are configured to detect the temperature of the thermoforming material 414 as the thermoforming material 414 is heated by the heaters 122, 124. In some embodiments, the temperature sensors 126 are surface temperature sensors configured to detect the temperature of the surface of an item (e.g., the thermoforming material 414, the dental mold 406). In some embodiments, the heating station 110 includes a single temperature sensor 126 designed or configured to detect the temperature of the thermoforming material 414 when the thermoforming material 414 is heated by the first heater 122 and subsequently heated by the second heater 124 (and to simultaneously or stepwise detect the temperature of additional thermoforming material at the first heater 122 while the thermoforming material 414 is at the second heater 124). In some embodiments, the heating station 110 includes at least two dedicated temperature sensors 126 for detecting the temperature of the thermoforming material 414 at the first heater 122 and the second heater 124, respectively.

In some embodiments, the heaters 122, 124 are independently controlled based on data from the temperature sensors 126. For instance, the heaters 122, 124 may slow down the heating process (e.g., by decreasing the level of heat output by a heater) as the temperature of the thermoforming material 414 approaches various thresholds, as described in greater detail below. Thus, the heaters 122, 124 may regulate the temperature of the thermoforming material 414.

The forming station 112 is shown to include an actuator 128 and a temperature sensor 126. The temperature sensor may be similar to or part of a same temperature sensor system as the temperature sensors 126 described above with respect to the heating station 110. In some embodiments, the controller 132 verifies that the temperature of the thermoforming material 414 proximate the forming station 112 is above a threshold temperature or within a temperature range before controlling the actuator 128 and the pressure system 138 to thermoform the thermoforming material 414 (e.g., a temperature substantially the same as the second temperature threshold that the thermoforming material 414 reaches at the first heater, less than the second temperature threshold). In some embodiments, if the temperature of the thermoforming material 414 proximate the forming station 112 does not pass the temperature verification, the thermoforming material 414 is not thermoformed and instead cycles back around the system 100 to be thermoformed on another pass through the forming station 112. In another embodiment, a technician can remove the non-thermoformed thermoforming material 414 if the thermoforming material 414 is compromised (e.g., overheated, sagging, deformed) and replace it with a new thermoforming material 414 to be thermoformed on another pass through the forming station 112.

The actuator 128 may be designed or configured to press together the heated thermoforming material 414 and the dental mold 406. The actuator 128 may be a pneumatic actuator 128, hydraulic actuator 128, etc. The actuator 128 may be configured to press together the heated thermoforming material 414 and dental mold 406.

In some embodiments, the actuator 128 presses together the thermoforming material 414 and dental mold 406 by lifting the dental mold 406 towards the thermoforming material 414. The actuator 128 is shown to include an upper chamber structure 134 and a lifting device 136. The upper chamber structure 134 may be sized to substantially match the size of the dental mold nest 404. Referring briefly to FIGS. 1-3 and 9, the lifting device 136 lifts the dental mold 406 upwardly towards the thermoforming material 414. The lifting device 136 extends through an opening 130 of the first motorized belt 102 in the bay 106 defined by the cleats 104. The opening 130 extends through the first motorized belt 102. The opening 130 may be sized similar to a size of the opening 408 in the thermoforming assembly 108. The lifting device 136 extends through both openings 130, 408, and lifts the dental mold nest 404 (with the dental mold 406 positioned therein) towards the thermoforming material 414.

As the lifting device 136 lifts the dental mold nest 404 towards the thermoforming material 414, the upper chamber structure 134 moves downwardly towards the dental mold nest 404. The upper chamber structure 134 and the dental mold nest 404 may have a similar shape and size such that the outer perimeter of the dental mold nest 404 is aligned with the lower perimeter of the upper chamber structure 134. The upper chamber structure 134 and dental mold nest 404 may together sandwich the thermoforming material 414. As the upper chamber structure 134 and dental mold nest 404 sandwich the thermoforming material 414, the upper chamber structure 134 and dental mold nest 404 are pushed together such that small opposing forces are exerted on the thermoforming material 414 to act as a seal between the upper chamber structure 134 and the dental mold nest 404. A lower chamber structure of the forming station 112 can apply pressure to an upper portion of the inner chamber or vacuum suction to the inner chamber (e.g., below the thermoforming material 414 and the dental mold 406 to pull the thermoforming material 414 down onto the dental mold 406.

In another embodiment, the upper chamber structure 134 may introduce pressurized air into the inner chamber (e.g., above the thermoforming material 414). For instance, the system 100 may include a pressure system 138 including reservoir 140 storing pressurized air, a hose 142 connecting the reservoir to the inner chamber (e.g., through the upper chamber structure 134), and a valve 144 for regulating pressurized air flow into the inner chamber. The valve 144 is opened when the inner chamber is formed to introduce pressurized air (for instance 80 psi to maintain a 50 psi pressure inside the inner chamber, though the pressure may range from 30 PSI to 100+ PSI in some embodiments) above the thermoforming material 414. As the pressurized air is introduced in the inner chamber (which is effectively sealed by the thermoforming material 414 at the juncture between the upper chamber structure 134 and dental mold nest 414), the thermoforming material 414 (which is softened, or in a glassy state) forms onto the dental mold 406.

In all embodiments, the dental mold 406 and thermoforming material 414 may thus have complementary surface contours (e.g., the thermoforming material 414 may become a negative impression of the dental mold 406).

Following the thermoforming material 414 forming onto the dental mold 406 within the inner chamber, the upper chamber structure 134 may be lifted up (or the dental mold nest 404 may be lowered) to remove the seal and return the inner chamber to a neutral pressure (e.g., atmospheric pressure). The thermoforming material 414 naturally cools, and the thermoforming assembly 108, including the thermoforming material 414 now thermoformed to the dental mold 406, is moved from the forming station 112. The thermoforming material 414 is thermoformed to the dental mold 406 in a duration corresponding to the duration for heating the thermoforming material 414 of subsequent thermoforming assemblies 108 at the first heater 122 and the second heater 124. Hence, each step in the thermoforming process may be controlled to take approximately the same duration such that various steps may not cause a bottleneck. Each thermoforming assembly 108 may advance within the thermoforming process together with other thermoforming assemblies 108 such that each thermoforming assembly 108 is processed in stages (e.g., similar to an assembly line).

The system 100 may include a controller 132. The controller 132 may be communicably coupled to the temperature sensor(s) 126, the motor 120 powering the motorized belt(s) 102, 114, the actuator 128, the transfer device(s) 116, 118, etc. The controller 132 may include a processor and memory. The processor may be a general purpose or specific purpose processor, an application specific integrated circuit (ASIC), one or more field programmable gate arrays (FPGAs), a group of processing components, or other suitable processing components. The processor may be configured to execute computer code or instructions stored in memory or received from other computer readable media (e.g., CDROM, network storage, a remote server, etc.) to perform one or more of the processes described herein. The memory may include one or more data storage devices (e.g., memory units, memory devices, computer-readable storage media, etc.) configured to store data, computer code, executable instructions, or other forms of computer-readable information. The memory may include random access memory (RAM), read-only memory (ROM), hard drive storage, temporary storage, non-volatile memory, flash memory, optical memory, or any other suitable memory for storing software objects and/or computer instructions. The memory may include database components, object code components, script components, or any other type of information structure for supporting the various activities and information structures described in the present disclosure. The memory may be communicably connected to the processor and may include computer code for executing (e.g., by the processor, etc.) one or more of the processes described herein.

The controller 132 may be designed or implemented to perform various functions. For instance, the controller 132 may receive data from the temperature sensor(s) 126, which may be used as feedback for controlling the motor 120 that powers/drives the motorized belt(s) 102, 114, the actuator 128, the transfer device(s) 116, 118, the heaters 122, 124, the pressure system 138, etc. The controller 132 may include various instructions, which may be stored on memory. Such instructions may be executed by the processor. Hence, the processor may execute instructions stored on memory and perform various functions associated therewith.

The controller 132 may be configured to position a thermoforming assembly 108 at the first heater 122. For instance, the controller 132 may control the motor 120 to advance a loaded thermoforming assembly 108 towards the transfer device 116. The controller 132 may control the transfer device 116 to push the loaded thermoforming assembly 108 from the second motorized belt 114 to the first motorized belt 102. The controller 132 can control the motor 120 to advance the loaded thermoforming assembly 108 underneath the first heater 122. In each instance where the motor 120 causes a thermoforming assembly 108 to advance, another thermoforming assembly/bay 108, 106 may advance within the system 100. Thus, the bays 106 moving in the system 100 may advance in unison such that, when one bay 106 advances, another bay 106 advances (e.g., in a stepwise or piecewise fashion).

In some embodiments, the controller 132 may activate the first heater 122 when the thermoforming assembly 108 is located underneath the first heater 122. In some embodiments, the first heater 122 may be maintained in an active state (e.g., the first heater 122 may output heat throughout the process). The first heater 122 heats the thermoforming material 414 located beneath the first heater 122. The temperature sensor 126 detects the temperature of the thermoforming material 414. The temperature sensor 126 generates data corresponding to the temperature of the thermoforming material 414, which is communicated to the controller 132. In some embodiments, the temperature sensor 126 generates such data in real-time or near real-time. For example, a current temperature of the thermoforming material 414 is generated by the temperature sensor 126 as the thermoforming material 414 is heated.

The controller 132 receives the data corresponding to the temperature of the thermoforming material 414. The controller 132 determines, based on the data from the temperature sensor 126, whether the temperature of the thermoforming material 414 meets a first temperature threshold. "Meets," as used herein with reference to a threshold, means satisfying a threshold (e.g., being the same as, falling within a range, exceeding a minimum, being less than a maximum, etc.). The first temperature threshold may be set by a dental aligner manufacturer/producer. The first temperature threshold may be static, or the first temperature threshold may be dynamic (e.g., based on the type of thermoforming material, the hardness of the thermoforming material, the thickness of the thermoforming material, etc.). The first temperature threshold may be, for instance, a range of temperatures. As one example, the first temperature threshold may be 120° F.-300° F. The first temperature threshold may be a threshold used for advancing the thermoforming assembly 108 from the first heater 122 to the second heater 124. When the controller 132 determines that the temperature of the thermoforming material 414 meets the first threshold, the controller 132 controls the motor 120 to advance the thermoforming assembly 108 from the first heater 122 to the second heater 124. When the controller 132 determines that the temperature of the thermoforming material 414 does not meet the first threshold (e.g., is less than the first threshold), the controller 132 maintains the thermoforming assembly 108 at the first heater 122 until the temperature of the thermoforming material 414 meets the first threshold.

The controller 132 advances the thermoforming assembly 108 from the first heater 122 to the second heater 124. In some embodiments, the second heater 124 may be similar to at least some aspects of the first heater 122. However, in some embodiments, the first heater 122 is operated differently than the second heater 124 (e.g., at a different temperature, for a different duration for each thermoforming assembly 108, applying a different temperature pattern). The second heater 124 similarly outputs heat to the thermoforming material 414. A temperature sensor 126 (described herein as the temperature sensor 126 though, in some embodiments, may be a dedicated temperature sensor for the second heater 124) detects a temperature of the thermoforming material 414 while the thermoforming material 414 is heated by the second heater 124. The controller 132 receives the data corresponding to the temperature of the thermoforming material 414. The controller 132 determines, based on the data from the temperature sensor 126, whether the temperature of the thermoforming material 414 meets a second temperature threshold. Similar to the first temperature threshold, the second temperature threshold may be set by a dental aligner manufacturer/producer. The second temperature threshold may be static, or the second temperature threshold may be dynamic. The second temperature threshold may be, for instance, a range of temperatures. As one example, the second temperature threshold may be 270° F.-350° F. The second temperature threshold may be a threshold used for advancing the thermoforming assembly 108 from the second heater 124 to the forming station 112. In some embodiments, the second temperature threshold may be greater than 300° F., but no greater than 350° F. Hence, the controller 132 determines that the temperature of the thermoforming material 414 meets the second threshold when the temperature is both (or either) greater than 300° F. and/or less than 350° F.

When the controller 132 determines that the temperature of the thermoforming material 414 meets the second threshold, the controller 132 controls the motor 120 to advance the thermoforming assembly 108 from the second heater 124 to the forming station 112. When the controller 132 determines that the temperature of the thermoforming material 414 does not meet the second threshold (e.g., is less than the lower limit of the second threshold), the controller 132 maintains the thermoforming assembly 108 at the second heater 124 until the temperature of the thermoforming 414 meeting the second threshold.

In some embodiments, the controller 132 controls the first heater 122 and second heater 124 based on data corresponding to the temperature of the thermoforming material 414 at the first heater 122 and/or the temperature of the thermoforming material 414 at the second heater 124. For instance, the controller 132 monitors the temperature of the thermoforming material 414 at the first heater 122 and the thermoforming material 414 at the second heater 124. In these embodiments, the controller 132 may increase the heat output from the first heater 122 where the thermoforming material 414 at the first heater 122 lags behind the first threshold and the thermoforming material 414 at the second heater 124 approaches the second threshold. Additionally, the controller 132 may decrease the heat output from the second heater 124 where the thermoforming material 414 at the first heater 122 lags behind the first threshold and the thermoforming material 414 at the second heater 124 approaches the second threshold. In each of these embodiments, the controller 132 regulates the heat output of the first heater 122 and/or second heater 124 based on the data corresponding to the temperature of the thermoforming material 414 at the first heater 122 and/or the thermoforming material 414 at the second heater 124. Such embodiments may lessen the likelihood of bottlenecks and overheating thermoforming material 414.

In some embodiments, the controller 132 controls the motor 120 to advance the thermoforming assemblies 108 based on the temperature of the thermoforming material 414 at the first heater 122 and/or the thermoforming material 414 at the second heater 124. In these embodiments, the controller 132 monitors data from the temperature sensors 126 to determine whether the thermoforming material 414 at the first heater 122 meets the first threshold and the thermoforming material 414 at the second heater 124 meets the second threshold. The controller 132 advances the thermoforming assemblies 108 when both thermoforming materials 414 at the first heater 122 and second heater 124 meet the respective thresholds. Where the temperature of one thermoforming material 414 meets one threshold but the temperature of the other thermoforming material 414 doesn't meet the other threshold, the controller 132 may control the corresponding heaters 122, 124 as described above (e.g., increase one heat output for one heater 122 and/or decrease heat output for the other heater 124).

When the thermoforming assembly 108 is located at the forming station, the controller 132 may generate a signal for the actuator 128. The controller 132 may communicate the signal to the actuator 128 for controlling the actuator 128. The controller 132 may control the actuator 128 to press together the heated thermoforming material 414 and the dental mold 406. The controller 132 controls the actuator 128 to press together the heated thermoforming material 414 and the dental mold 408 for a duration of time (e.g., a number of seconds, minutes, etc.) for sufficiently thermoforming the thermoforming material 414 to the dental mold 408. The controller 132 may control the upper chamber structure 134 and lifting device 136 to form a seal between the lower perimeter of the upper chamber structure 134 and the dental mold nest 404. The controller 132 controls the pressure system 138 to pressurize (e.g., via pressure system 138) the inner chamber formed by the upper chamber structure 134 and the dental mold nest 404. As the inner chamber is pressurized, the thermoforming material 414 forms around the dental mold 406 (e.g., thereby thermoforming the thermoforming material 414 to the dental mold 406). Following thermoforming of the thermoforming material 414 to the dental mold 408, the controller 132 advances the thermoforming assembly 108 to subsequent stations for pushing the thermoforming assembly 108 with the dental aligners positioned thereon (or following the dental aligners being removed) from the first motorized belt 102 to the second motorized belt 114, and reloading (e.g., by an operator) additional dental molds 408 and thermoforming material 414. Hence, the thermoforming assemblies 108 may be re-used for thermoforming additional dental aligners.

Figure 10:
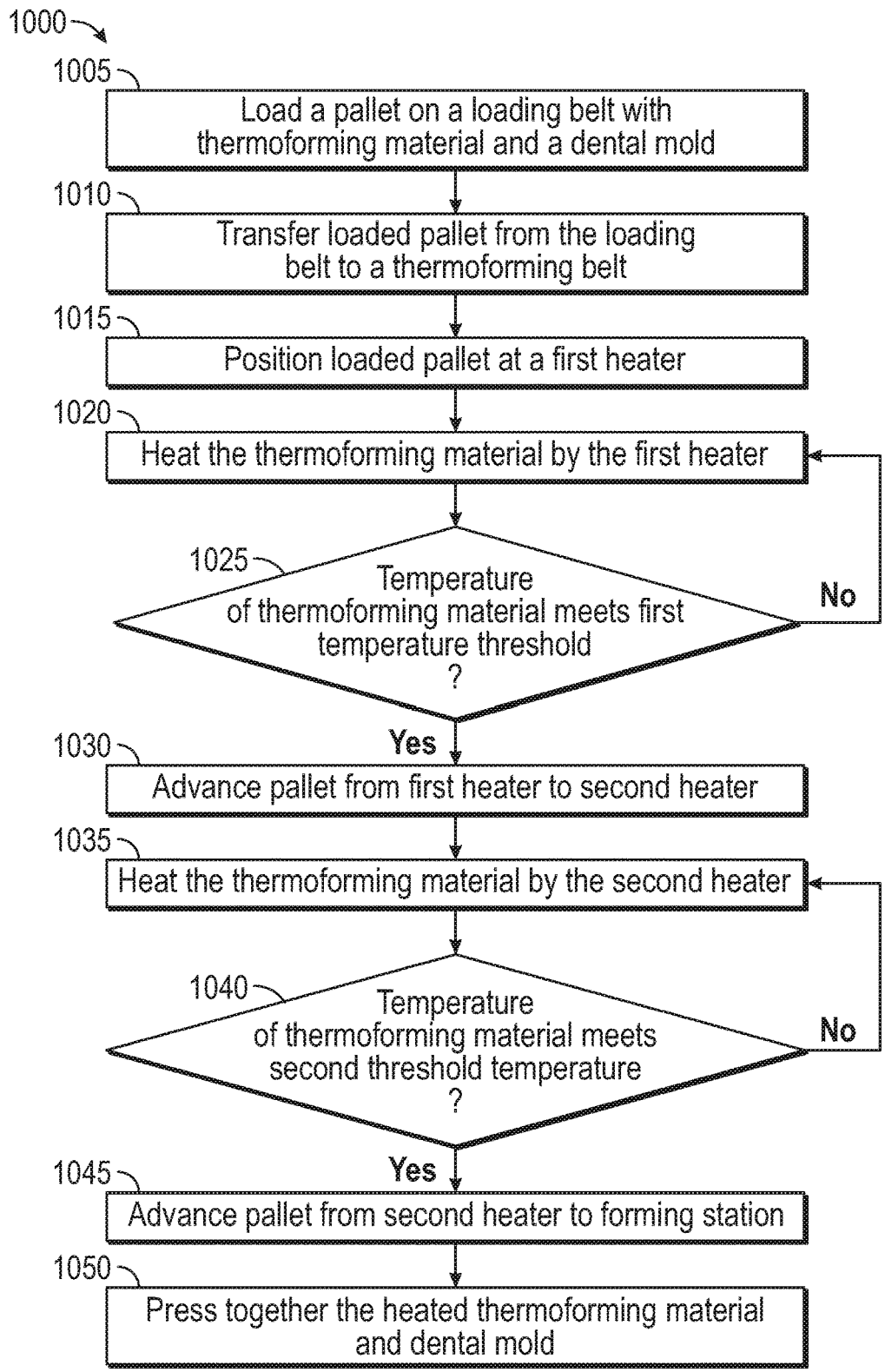
FIG. 10 is a flowchart of an example method of thermoforming dental aligners, according to an exemplary embodiment.

Referring to FIG. 10, a flowchart is depicted showing a method 1000 of thermoforming dental aligners, according to an exemplary embodiment.

The method 1000 begins at operation 1005. At operation 1005, a thermoforming assembly 108 is loaded with thermoforming material 414 and a dental mold 406. The thermoforming assembly 108 may be positioned on a loading belt, such as the second motorized belt 114. The same thermoforming assembly 108 may have previously contained thermoforming material 414 and a different dental mold 406 and underwent a prior thermoforming operation. Hence, thermoforming assemblies 108 may be reused or recycled through the system 100 described above. In some embodiments, the thermoforming assembly 108 is loaded by an operator. In some embodiments, the thermoforming assembly 108 is loaded automatically (e.g., by various articulated arms, robotic controls, etc.).

The thermoforming assembly 108 may generally be assembled while on the loading belt, such as the second motorized belt 114. An operator may remove the retaining ring 420, place the thermoforming material 414 on the thermoforming material nest 416, and re-attach the retaining ring 420. Additionally, the operator may add the dental mold 406 to the dental mold nest 404.

At operation 1010, the loaded thermoforming assembly 108 is transferred from the loading belt to a thermoforming belt, such as the first motorized belt 102. In some embodiments, the transfer device 116 transfers the thermoforming assembly 108 from the loading belt to the thermoforming belt. The controller 132 controls the transfer device 116 to push the thermoforming assembly 108 between the cleats 104 on the thermoforming belt.

At operation 1015, the thermoforming assembly 108 (e.g., including thermoforming material 414 and a dental mold 406) is positioned at a first heater 122. The controller 132 controls a motor 120 for the first motorized belt 102 to move the thermoforming assembly 108 to the first heater 122 (e.g., beneath the first heater 122). As the controller 132 controls the motor 120 for the first motorized belt 102, each thermoforming assembly on the first motorized belt 102 are correspondingly advanced. The controller 132 may control the motor 120 in steps. For instance, the controller 132 may control the motor 120 to move the first motorized belt 102 a predetermined distance sufficient to move a thermoforming assembly 108 from one station to another station, and pause for a predetermined or controlled duration. Hence, each thermoforming assembly 108 may advance within the system substantially in unison to prevent or eliminate bottlenecks.

At operation 1020, the first heater 122 heats the thermoforming material 414. The first heater 122 heats the thermoforming material 414 located beneath the first heater 122. In some embodiments, the controller 132 controls the heat output of the first heater 122. For instance, the controller 132 may control the heat output of the first heater 122 based on the temperature of the thermoforming material 414 at the first heater 122 (e.g., lower the heat output of the first heater 122 as the temperature of the thermoforming material 414 approaches the first temperature threshold when the temperature of the thermoforming material 414 at the second heater 124 is not approaching the second temperature threshold).

At operation 1025, the controller 132 determines whether the temperature of the thermoforming material 414 meets a first temperature threshold. The first temperature threshold may be a fixed temperature threshold. The fixed temperature threshold may depend on the type of material. In some embodiments, the first temperature threshold may correspond to the second temperature threshold described below (e.g., in reference to operation 1040). For instance, the first temperature threshold may be half of (or approximately half of) the second temperature threshold.

In some embodiments, the controller 132 determines that the temperature of the thermoforming material 414 meets the first temperature threshold while the thermoforming assembly 108 including the thermoforming material 414 and the dental mold 406 are located at the first heater 122. The controller 132 determines whether the temperature of the thermoforming material 414 meets the first temperature threshold based on the data from the temperature sensor 126 configured to detect a temperature of the thermoforming material 414 at the first heater 122 of the heating station 110. When the controller 132 determines the temperature of the thermoforming material 414 does not meet the first temperature threshold, the controller 132 may maintain the position of the thermoforming assembly 108 at the first heater 122 (e.g., the first heater 122 may continue to heat the thermoforming material 414). Hence, the method 1000 may return to operation 1020 until the temperature of the thermoforming material 414 meets the first temperature threshold.

In some embodiments, the first temperature threshold may be a range of temperatures. For instance, the temperature of the thermoforming material 414 may meet the first temperature threshold if the temperature of the thermoforming material 414 falls within the range of temperatures. The range of temperatures may be, for instance, 140° F.-200° F.

In some embodiments, the range of temperatures (or first temperature threshold) may be a static threshold. In some embodiments, the range of temperatures (or first temperature threshold) may be a dynamic threshold. The threshold may be set by the dental aligner manufacturer/producer. The threshold may correspond to the type of thermoforming material 414. For instance, the threshold may be higher for thicker and/or harder thermoforming materials 414 (e.g., having a higher elastic modulus), and may be thinner and/or lower for softer thermoforming materials 414 (e.g., having a lower elastic modulus). As another example, the threshold may be different for thermoforming material 414 having various chemical compositions which may contribute to different melting/softening points for proper thermoforming. The controller 132 receives the temperature readings from the temperature sensor(s) 126. The controller 132 compares the temperature to the first temperature threshold to determine whether the temperature of the thermoforming material 414 meets the first temperature threshold.

At operation 1030, the controller 132 advances the thermoforming assembly 108 from the first heater 122 to the second heater 124. In some embodiment, the controller 132 controls a motor 120 of the first motorized belt 102 upon which the thermoforming assembly 108 is located to advance the thermoforming assembly 108 from the first heater 122 to the second heater 124 at the heating station 110. The controller 132 communicates a signal to the motor 120 which causes the motor to rotate the first motorized belt 102 (e.g., in the direction A). The motor 120 causes the first motorized belt 102 to advance the thermoforming assembly 108 to the second heater 124. The controller 132 advances the thermoforming assembly 108 from the first heater 122 to the second heater 124 responsive to the controller 132 determining that the temperature of the thermoforming material 414 meets the first temperature threshold.

At operation 1035, the thermoforming material 414 is heated by the second heater 124. The first heater 124 heats the thermoforming material 414 located beneath the second heater 124. In some embodiments, the controller 132 controls the heat output of the second heater 124. For instance, the controller 132 may control the heat output of the second heater 124 based on the temperature of the thermoforming material 414 at the second heater 124 (e.g., increase the output of the second heater 124 where the temperature of the thermoforming material 414 is not sufficiently approaching the second temperature threshold when the temperature of the thermoforming material 414 at the first heater 122 is approaching the first temperature threshold).

At operation 1040, the controller 132 determines whether the temperature of the thermoforming material 414 meets a second temperature threshold. In some embodiments, the controller 132 determines that the temperature of the thermoforming material 414 meets the second temperature threshold while the thermoforming assembly 108 is located at the second heater 124. The controller 132 determines the temperature of the thermoforming material 414 meets the second temperature threshold based on data from the temperature sensor 126. Accordingly, operation 1020 may be similar to operation 1010. When the controller 132 determines the temperature of the thermoforming material 414 does not meet the second temperature threshold, the controller 132 maintains the position of the thermoforming assembly 108 at the second heater 124. Hence, the method 1000 may return to operation 1035 until the temperature of the thermoforming material 414 meets the second temperature threshold.

In some embodiments, the second temperature threshold may be a range of temperatures. For instance, the temperature of the thermoforming material 414 may meet the second temperature threshold if the temperature of the thermoforming material 414 falls within the range of temperatures. The range of temperatures may be, for instance, 270° F.-350° F. In some embodiments, the range of temperatures (or second temperature threshold) may be a static threshold. In some embodiments, the range of temperatures (or second temperature threshold) may be a dynamic threshold. The threshold may be set by the dental aligner manufacturer/producer. In some embodiments, the threshold may correspond to the type of thermoforming material 414. For instance, the threshold may be higher for harder/thicker thermoforming materials 414, and may be lower for softer/thinner thermoforming materials 414. The controller 132 receives the temperature readings from the temperature sensor(s) 126. The controller 132 compares the temperature to the second temperature threshold to determine whether the temperature of the thermoforming material 414 meets the second temperature threshold.

At operation 1045, the controller 132 advances the thermoforming assembly 108 from the second heater 124 to the forming station 112. In some embodiments, the controller 132 controls the motor 120 of the first motorized belt 102 to advance the thermoforming assembly 108 from the second heater 124 to the forming station 112. The controller 132 communicates a signal to the motor 120 which causes the motor to rotate the first motorized belt 102 (e.g., in the direction A). The motor 120 causes the first motorized belt 102 to advance the thermoforming assembly 108 to the forming station. The controller 132 advances the thermoforming assembly 108 from the second heater 124 to the forming station 112 responsive to the controller 132 determining that the temperature of the thermoforming material 414 meets the second temperature threshold.

At operation 1050, an actuator 128 presses together the heated thermoforming material 414 and the dental mold 406. In some embodiments, the controller 132 controls the actuator 128 and the pressure system 138 at the forming station 112 to press together the heated thermoforming material 414 and the dental mold 406 to thermoform the thermoforming material 414 to the dental mold 406. In some embodiments, the actuator 128 is controlled mechanically, using pneumatic pressure, using a vacuum, using hydraulics, or any combination thereof. In some embodiments, the pressure system 138 controls movement of the actuator 128. The controller 132 controls the actuator 128 responsive to determining that the temperature of the thermoforming material 414 meets the third temperature threshold (e.g., a temperature for thermoforming the thermoforming material 414, a temperature substantially the same as the second temperature threshold, a temperature less than the second temperature threshold) and the thermoforming assembly 108 is positioned at the forming station 112. Hence, the controller 128 controls the actuator 128 when the thermoforming assembly 108 is suitably located at the forming station 112.

The actuator 128 includes an upper chamber structure 134 and a lifting device 136. The controller 132 controls the lifting device 136 to lift the dental mold nest 404 with the dental mold 406 towards the thermoforming material 414. The controller 132 controls the upper chamber structure 134 to move downwardly towards the thermoforming material 414. The upper chamber structure 134 is aligned with the dental mold nest 404 such that the upper chamber structure 134 and dental mold nest 404 sandwich the thermoforming material 414. The thermoforming material 414 acts as a seal.

The controller 132 controls the pressure system 138 to depressurize the inner chamber formed by the upper chamber structure 134 and the dental mold 404. In another embodiment, pressurized air may be introduced through the upper chamber structure 134 to pressurize the air above the thermoforming material 414, causing the thermoforming material 414 to thermoform to the dental mold 406. It will be appreciated that either or both negative air pressure (e.g., applied via a vacuum from the bottom of the chamber), and positive air pressure (e.g., applied from the top of the chamber), can be applied to the chamber to cause the thermoforming material 414 to mold onto the dental mold 406, thereby resulting in a thermoformed dental aligner. The dental mold 406 and thermoforming material 414 thus have complementary surface contours (e.g., the thermoforming material 414 may become a negative impression of the dental mold 406).

In some embodiments, the method 1000 further includes transferring the thermoforming assembly 108 including the thermoforming material 414 and dental mold 406 from the thermoforming belt (e.g., the second motorized belt 114) to the loading belt (e.g., the first motorized belt 102), where the thermoforming assemblies 108 may be loaded (e.g., by an operator), and then transferred back on the first motorized belt 102 for thermoforming. When unloading a thermoforming assembly 108, an operator may remove the dental aligner and dental mold 306 (which may be stuck together) and then reload the thermoforming assembly 108 by adding a new dental mold 306 and new thermoforming material 414, before the reloaded thermoforming assembly 108 is transferred back to onto the first motorized belt 102 for thermoforming.

In one or more embodiments, the method 1000 described above may be used for creating a set of aligners where each aligner corresponds to the same dental mold 406 but has a different thickness and/or hardness (e.g., as indicated by an elastic modulus). In some embodiments, the set of aligners may be created by separate systems 100. In some embodiments, the set of aligners may be created by the same system 100. Each of these embodiments will be described in greater detail below.

As described above, the set of aligners may have different hardness and/or different thicknesses. For instance, a set of aligners may correspond to two or more aligners constructed of different types of thermoforming material 414. The aligners may be constructed of a softer and/or thinner thermoforming material 414, a thermoforming material 414 of an intermediate hardness and/or thickness, and a harder and/or thicker thermoforming material 414 (relative to one another). In some embodiments, the aligners may be constructed of different materials having material properties other than or in addition to a hardness or thickness of the material, such as a chemistry of the material, a shape of the material, a color of the material, or other unique material property. Each of the thermoforming materials 414 have corresponding characteristics, such as thermoforming temperature, which are used by the system 100 for creating the aligners. The soft/thin aligner, the intermediate hardness/ thickness aligner, and the hard/thick aligner are each used in stages for repositioning the user's teeth. For example, a user can be instructed to first wear a soft and/or thin aligner of the set for a first time period, to then wear the intermediate hardness and/or thickness aligner of the set for a second time period, and then wear the hard and/or thick aligner of the set for a third time period. The time periods may be the same (e.g., one week, two weeks, three weeks) or different. For example, any of the softer and/or thinner, intermediate hardness and/or thickness, and hard and/or thick aligners can be worn for either a shortest or longest time period (e.g., the soft/thin aligner is worn for a shorter duration than the aligner of intermediate hardness/thickness and the hard/ thick aligner). The soft/thin aligner can provide a lowest amount of force to the user's teeth, the intermediate hardness/thickness aligner can provide an intermediate amount of force to the user's teeth, and the hard/thick aligner can provide a greatest amount of force to the user's teeth. A such, the force level or pressure level exerted by the aligners on the user's teeth can vary according to a characteristic of the material that the aligner is made from.

The aligners may be generated using the system 100 described above. In some embodiments, various components of the system 100, such as the heaters 122,124 and pressure system 138, may be adjusted based on the type of the thermoforming material 144. For instance, the temperature thresholds may be modified based on the type of thermoforming material 414. The temperature thresholds may be increased for harder/thicker thermoforming materials 414, and decreased for softer/thinner thermoforming materials 414. Hence, the duration at which the thermoforming material 414 is heated by a respective heater (or the heat output of a respective heater) may be changed based on the type of the thermoforming material. In some embodiments, the pressure inside the inner chamber formed by the upper chamber structure 134 and the dental mold nest 404 may be adjusted based on the type of thermoforming material 414. For instance, the pressure may be increased inside the inner chamber for harder/thicker thermoforming materials 414, and may be decreased inside the inner chamber for softer/ thinner thermoforming materials 414, or vice versa. In each of these embodiments, the characteristics of the components of the system 100 may correspond to the type of thermoforming material 414.

In some embodiments, one system 100 may be used for producing a set of aligners. For instance, the components within a single system 100, such as the heaters 122, 124, the pressure system 138, etc. are adjusted based on the type of thermoforming material 414. The controller 132 may receive an input (e.g., from an operator) corresponding to the type of thermoforming material 414 (e.g., identifying the specific material, the hardness, the thickness, a category, etc.) or the controller 132 may receive an input from an indicator on the mold 406. The controller 132 selects parameters, including heater temperature, pressure, etc. based on the type of thermoforming material 414. In this regard, the controller 132 dynamically adjusts components within the system 100 in accordance with the type of thermoforming material 414. The operator may assemble one thermoforming assembly 108 using a first thermoforming material and a dental mold, initiate the thermoforming process on the system 100, remove the first thermoforming material thermoformed to the dental mold, and repeat the thermoforming process using a second (and subsequent) thermoforming material with the same dental mold and the same system 100.

In some embodiments, a plurality of systems 100 may be used for producing a set of aligners. For instance, each component within a respective system 100 may be configured for thermoforming a particular type of thermoforming material 414. The heaters 122, 124 output a preset heat output, the pressure system 138 depressurizes the inner chamber to a preset pressure, etc., in accordance with a particular type of thermoforming material 414. An operator may assemble one thermoforming assembly 108 using a first thermoforming material and a dental mold and initiate the thermoforming process on a first system 100. The operator may remove the thermoformed first thermoforming material, reassemble a thermoforming assembly with a second thermoforming material and the same dental mold, and initiate the thermoforming process on a second system 100.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to any precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below") are merely used to describe the orientation of various elements in the Figures. It should be noted that the orientation of various elements may differ according to other exemplary embodiments, and that such variations are intended to be encompassed by the present disclosure.

The hardware and data processing components used to implement the various processes, operations, illustrative logics, logical blocks, modules and circuits described in connection with the embodiments disclosed herein may be implemented or performed with a general purpose single- or multi-chip processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, such as a combination of a DSP and a microprocessor, a plurality of microprocessors, one or more microprocessors in conjunction with a DSP core, or any other such configuration. In some embodiments, particular processes and methods may be performed by circuitry that is specific to a given function. The memory (e.g., memory, memory unit, storage device) may include one or more devices (e.g., RAM, ROM, Flash memory, hard disk storage) for storing data and/or computer code for completing or facilitating the various processes, layers and modules described in the present disclosure. The memory may be or include volatile memory or non-volatile memory, and may include database components, object code components, script components, or any other type of information structure for supporting the various activities and information structures described in the present disclosure. According to an exemplary embodiment, the memory is communicably connected to the processor via a processing circuit and includes computer code for executing (e.g., by the processing circuit or the processor) the one or more processes described herein.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps. It is important to note that the construction and arrangement of the systems and methods of thermoforming dental aligners as shown in the various exemplary embodiments is illustrative only. Additionally, any element disclosed in one embodiment may be incorporated or utilized with any other embodiment disclosed herein. It should be appreciated that other elements of the various embodiments may be incorporated or utilized with any of the other embodiments disclosed herein.

What is claimed is:

1. A system comprising:
a plurality of thermoforming assemblies each configured to support a dental mold and a thermoforming material;
a heating system including a first heater, a second heater, and a temperature sensor, the first heater configured to heat the thermoforming material when the thermoforming material is proximate the first heater, the second heater configured to heat the thermoforming material when the thermoforming material is proximate the second heater, the temperature sensor arranged to detect a temperature of the thermoforming material when the thermoforming material is proximate either of the first heater and the second heater;
a forming system including an actuator and a pressure system, the actuator configured to form a chamber encompassing the dental mold and a portion of the heated thermoforming material, the pressure system configured to apply pressure to the chamber to compress the heated thermoforming material to the dental mold; and
a conveyor system configured to move the plurality of thermoforming assemblies in a stepwise movement sequence from a loading area to the heating system, then from the heating system to the forming system, and then from the forming system to an unloading area, wherein each stepwise movement of the thermoforming assemblies is based on a temperature of a first thermoforming material of a first thermoforming assembly at the first heater and a temperature of a second thermoforming material of a second thermoforming assembly at the second heater.

2. The system of claim 1, further comprising a controller configured to control the first heater to heat the first thermoforming material above a first temperature threshold or within a first temperature range while simultaneously controlling the second heater to heat the second thermoforming material above a second temperature threshold or within a second temperature range.

3. The system of claim 1, wherein each thermoforming assembly includes a first support, a second support, a third support, and a separator, the first support configured to support the second support, the second support configured to support a dental mold, the third support configured to support thermoforming material, the separator configured to keep the dental mold separated from the thermoforming material prior to the thermoforming assembly interacting with the forming system.

4. The system of claim 3, wherein the thermoforming assembly further comprises a coupling mechanism configured to couple the thermoforming assembly with a motorized belt of the conveyor system to hold the thermoforming assembly in place on the motorized belt during interaction with the heating system and the forming system.

5. The system of claim 4, wherein the coupling mechanism comprises a notch on the first support, the notch configured to engage with a cleat fixed to the motorized belt.

6. The system of claim 4, wherein the second support is configured to be pushed by a lower component of the actuator upwardly away from the first support towards the third support to engage with an upper component of the actuator to bring the dental mold in contact with the thermoforming material and to form the chamber.

7. The system of claim 3, wherein each thermoforming assembly further includes a retaining ring configured to be removably secured to the third support to secure the thermoforming material to the third support.

8. The system of claim 1, wherein the pressure system is configured to apply pressure to the chamber to cause a pressure level of the chamber to reach a threshold pressure based on a type of the thermoforming material.

9. The system of claim 1, wherein the heating system is configured to heat the thermoforming material based on a type of the thermoforming material.

10. The system of claim 1, wherein the conveyor system comprises a first motorized belt and a second motorized belt, the first motorized belt configured to move the plurality of thermoforming assemblies to the heating system and from the heating system to the forming system, the second motorized belt defining the loading area and the unloading area.

11. The system of claim 10, further comprising a first transfer device and a second transfer device, the first transfer device configured to transfer the plurality of thermoforming assemblies from the second motorized belt to the first motorized belt, the second transfer device configured to transfer the plurality of thermoforming assemblies from the first motorized belt to the second motorized belt.

12. The system of claim 1, wherein the portion of the heated thermoforming material is a first portion, and wherein the chamber is formed by compressing a second portion of the heated thermoforming material between an upper component of the forming system and a support of the thermoforming assembly configured to support the dental mold.

13. A system comprising:
a controller configured to:
control a conveyor system to move a thermoforming assembly in a stepwise movement sequence, the thermoforming assembly comprises a dental mold and a thermoforming material, the stepwise movement sequence comprises moving the assembly in sequence to a first predetermined position proximate a first heater, then to a second predetermined position proximate a second heater, then to a third predetermined position proximate a forming system, wherein the thermoforming assembly remains at each predetermined position for a predetermined time;
control the first heater to heat the thermoforming material above a first temperature threshold or within a first temperature range;
control the second heater to heat the thermoforming material above a second temperature threshold or within a second temperature range; and
control the forming system to compress the heated thermoforming material to the dental mold to form a shape of a dental aligner based on the thermoforming material being above a forming temperature threshold or within a forming temperature range.

14. The system of claim 13, wherein the forming system is configured to form an at least substantially airtight chamber around the dental mold and a first portion of the heated thermoforming material by using a second portion of the heated thermoforming material to form a substantially airtight seal.

15. The system of claim 14, wherein the substantially airtight seal is formed by compressing the second portion of the heated thermoforming material between an upper component of the forming system and a support of the thermoforming assembly configured to support the dental mold.

16. The system of claim 15, wherein the controller is further configured to control a pressure system to pressurize the chamber to cause the first portion of the heated thermoforming material to compress onto the dental mold.

17. The system of claim 13, wherein the controller is further configured to control the at least one of the first heater, the second heater, and the forming system based on a characteristic of the thermoforming material.

18. The system of claim 17, wherein the characteristic of the thermoforming material is a hardness or thickness.

19. A method comprising:
  determining, based on data from a temperature sensor configured to detect a temperature of a thermoforming material at a first heater of a heating system, that the temperature of the thermoforming material meets a first temperature requirement while a thermoforming assembly including the thermoforming material and a dental mold is located at the first heater;
  controlling a conveyor system coupled with the thermoforming assembly to advance the thermoforming assembly from the first heater to a second heater of the heating system;
  determining, based on data from the temperature sensor, that the temperature of the thermoforming material meets a second temperature requirement while the thermoforming assembly is located at the second heater;
  controlling the conveyor system to advance the thermoforming assembly from the second heater to a forming system; and
  controlling a forming system including an actuator and a pressure system to apply pressure to a chamber around the dental mold and at least a portion of the thermoforming material to compress the thermoforming material to the dental mold.

20. A system comprising:
  a first thermoforming system comprising a first heating system and a first forming system, the first heating system configured to heat a first thermoforming material above a first temperature threshold or within a first temperature range, the first forming system configured to compress the first thermoforming material to a dental mold to form a first dental aligner having a first hardness or a first thickness;
  a second thermoforming system comprising a second heating system and a second forming system, the second heating system configured to heat a second thermoforming material above a second temperature threshold or within a second temperature range, the second forming system configured to compress the second thermoforming material to the dental mold to form a second dental aligner having a second hardness or a second thickness; and
  a third thermoforming system comprising a third heating system and a third forming system, the third heating system configured to heat a third thermoforming material above a third temperature threshold or within a third temperature range, the third forming system configured to compress the third thermoforming material to the dental mold to form a third dental aligner having a third hardness or a third thickness.

* * * * *